United States Patent [19]

Humphreys et al.

[11] Patent Number: 4,701,532
[45] Date of Patent: Oct. 20, 1987

[54] METHOD OF SELECTIVELY CHLORINATING 2-CHLORO-5-(TRICHLOROMETHYL) PYRIDINE IN THE 3-POSITION

[75] Inventors: Paula L. Humphreys, San Ramon; Thomas J. Dietsche, Berkeley; James L. Bixby, Pleasant Hill, all of Calif.

[73] Assignee: The Dow Chemical Company, Midland, Mich.

[21] Appl. No.: 844,647

[22] Filed: Mar. 27, 1986

Related U.S. Application Data

[63] Continuation-in-part of Ser. No. 718,610, Apr. 1, 1985, abandoned, which is a continuation-in-part of Ser. No. 655,200, Sep. 28, 1984, abandoned, which is a continuation-in-part of Ser. No. 479,056, Mar. 25, 1983, abandoned.

[51] Int. Cl.$^4$ .......................................... C07D 213/61
[52] U.S. Cl. .................................................. 546/345
[58] Field of Search ........................................ 546/345

[56] References Cited

U.S. PATENT DOCUMENTS

| | | | |
|---|---|---|---|
| 3,186,994 | 6/1965 | Johnston et al. | 546/345 |
| 3,420,833 | 1/1969 | Taplin, III | 546/248 X |
| 4,205,175 | 5/1980 | Bowden et al. | 546/345 |
| 4,241,213 | 12/1980 | Nishiyama et al. | 546/345 |
| 4,256,894 | 3/1981 | Dietsche et al. | 546/345 |
| 4,309,548 | 1/1982 | Wilson et al. | 546/345 |
| 4,331,811 | 5/1982 | Werner et al. | 546/345 |
| 4,483,993 | 11/1984 | Marinak et al. | 546/345 |
| 4,563,531 | 1/1986 | Marinak et al. | 546/345 |
| 4,564,681 | 1/1986 | Marinak et al. | 546/345 |
| 4,577,027 | 3/1986 | Marinak et al. | 546/345 |

*Primary Examiner*—Joseph Paul Brust
*Attorney, Agent, or Firm*—Merlin B. Davey

[57] ABSTRACT

The selective chlorination of 2-chloro-5-(trichloromethyl)pyridine in the 3-position is achieved by reacting 2-chloro-5-(trichloromethyl)pyridine in the liquid phase with an effective amount of Cl$_2$ at an elevated pressure and elevated temperature in the absence of an added catalyst.

11 Claims, No Drawings

METHOD OF SELECTIVELY CHLORINATING 2-CHLORO-5-(TRICHLOROMETHYL) PYRIDINE IN THE 3-POSITION

CROSS-REFERENCE TO RELATED APPLICATION

This application is a continuation-in-part of Ser. No. 718,610 filed Apr. 1, 1985, now abandoned, which in turn, is a continuation-in-part Ser. No. 655,200 filed Sept. 28, 1984, now abandoned, which in turn, is a continuation-in-part of Ser. No. 479,056 filed Mar. 25, 1983, and now abandoned.

BACKGROUND OF THE INVENTION

The present invention relates to a method of selectively chlorinating the 3-position of 2-chloro-5-(trichloromethyl)pyridine by a non-catalyzed, liquid phase chlorination reaction resulting in the formation of 2,3-dichloro-5-(trichloromethyl)pyridine.

2,3-Dichloro-5-(trichloromethyl)pyridine is a well known compound useful as an intermediate in the preparation of agricultural chemicals, such as, for example, 2-(4-((3-chloro-5-trifluoromethyl)-2-pyridinyl)oxy)-phenoxy propionic acid and derivatives thereof. Known methods of preparing 2,3-dichloro-5-(trichloromethyl)pyridine usually involve the use of a catalyst in a liquid phase chlorination reaction. See U.S. Pat. No. 4,331,811 which teaches and claims the use of tungsten, molybdenum and ruthenium catalysts.

SUMMARY OF THE INVENTION

Briefly, in accordance with the present invention, 2-chloro-5-(trichloromethyl)pyridine is contacted with chlorine ($Cl_2$) in the liquid phase in the absence of a tungsten, molybdenum or ruthenium catalyst under certain elevated temperature and pressure conditions to selectively chlorinate the 3-position of the pyridine ring. The present process can be conducted in a continuous, cyclical operation or in batch operation to produce 2,3-dichloro-5-(trichloromethyl)pyridine in a commercially viable yield and, preferably, in a ratio to 2,6-dichloro-3-(trichloromethyl)pyridine of at least 2.8:1.

One advantage of the present invention is that no catalyst need be employed, thus eliminating the cost of the catalyst, such as those employed in U.S. Pat. No. 4,331,811, and the additional catalyst removal step. It has been unexpectedly found that reacting 2-chloro-5-(trichloromethyl)pyridine in the liquid phase with $Cl_2$ under certain elevated temperature and pressure conditions in the absence of a catalyst selectively chlorinates the 3-position of the pyridine ring yielding 2,3-dichloro-5-(trichloromethyl)pyridine. Additionally, the absence of a catalyst reduces tar formation in the reaction vessel. Further, it has been found that when employing the particular temperature and pressure conditions of this invention, iron catalysts, such as $FeCl_3$, may be employed to increase the reaction rate without destroying the desired selectivity.

DETAILED DESCRIPTION OF THE INVENTION

In conducting the method of the present invention, gaseous chlorine ($Cl_2$) is passed into liquid 2-chloro-5-(trichloromethyl)pyridine at an elevated temperature and an elevated pressure. A solvent, such as chlorinated hydrocarbons, may optionally be employed but it is preferred to conduct the present reaction neat. An amount of chlorine ($Cl_2$) gas reactant is employed that is sufficient to selectively chlorinate the 3-position of the pyridine starting material. Usually at least about an equimolar amount of chlorine, based on the molar amount of 2-chloro-5-(trichloromethyl)pyridine, is employed. An excess of up to about 10 molar proportions or more of chlorine per mole of pyridine starting material is desirably employed. The most suitable rate at which the chlorine gas is fed into the reaction will vary with such factors as reaction temperature, pressure, reaction mixture volume, etc. and is readily determinable to one skilled in the art.

Certain elevated temperature and pressure are critical elements of the present invention. Temperatures in the range of from about 60 to about 180° C. are required while it is advantageous to conduct the present reaction at a temperature of from about 120° to about 170° C. A preferred temperature range in which to carry out the present reaction is from about 140° C. to about 160° C. and most preferably at about 150° C. The present reaction is advantageously run at superatmospheric pressures of from about 50 psig to about 1,000 psig. Higher pressures may be employed but, from an economic standpoint, are usually cost prohibitive. A preferred pressure range is from about 100 psig to about 300 psig. A particularly preferred pressure to run the present reaction is about 200 psig.

It has further been found that improved conversions are obtained when HCl is continuously added to the reaction mixture.

It has also been unexpectedly found that when employing the particular temperature and pressure conditions of the present invention, the desired selectivity to the production of 2,3-dichloro-5-(trichloromethyl)pyridine is obtained whether or not iron is present. Thus the presently claimed process may be carried out in iron reactors, if desired, and in the presence of $FeCl_3$ catalyst, optionally up to 3 weight percent or more ferric chloride catalyst.

In carrying out the present invention, 2-chloro-5-(trichloromethyl)pyridine, usually in the liquid form (about 53° C.), is preferably added to a reaction vessel, heated to between 60° and 180° C. and chlorine flow is commenced, usually at a sufficient rate to pressurized the reaction vessel to about 15 psig or more. The reaction is continued until sufficient amounts of 2,3-dichloro-5-(trichloromethyl)pyridine are obtained. Samples from the reaction vessel and vent gases are periodically taken and analyzed, employing known methods, to monitor the course of the reaction. The reaction is terminated by stopping the heating of the reaction vessel and the flow of chlorine thereto and allowing the reaction vessel pressure to drop to atmospheric pressure. The desired 2,3-dichloro-5-(trichloromethyl)pyridine is then recovered employing known separatory or purification techniques such as distillation, crystal refining or recrystallization from a solvent.

It is readily apparent to one skilled in the art that the reaction be run for an amount of time which maximizes the yield of 2,3-dichloro-5-(trichloromethyl)pyridine. The optimum reaction time will depend on a variety of factors, such as, for example, specific starting materials employed, pressure, temperature, amounts of reactants employed, and rate of the chlorine feed to name a few. Each operation of the present invention is monitored as described above to determine the optimum reaction time for that particular operation.

In one embodiment of the present invention, substantially pure 2-chloro-5-(trichloromethyl)pyridine is reacted with chlorine at a temperature of about 150° C. and at a pressure of about 200 psig. The 2,3-dichloro-5-(trichloromethyl)pyridine product is distilled from the reaction mixture.

Alternatively, the 2-chloro-5-(trichloromethyl)pyridine starting material is supplied as one component of a mixture of chlorinated β-picolines and chlorinated pyridines. The mixture is the reaction product resulting from the vapor phase chlorination of β-picoline which is used to prepare 2-chloro-5-(trichloromethyl)pyridine. This mixture typically contains the following compounds on a weight percent (wt. %) basis:

|   | Wt. % |
|---|---|
| 2-chloro-5-(trichloromethyl)pyridine | 20–35 |
| 2,6-dichloro-5-(trichloromethyl)pyridine | 30–40 |
| 2,3,6-trichloropyridine | 15–30 |
| other chlorinated β-picolines | 10–25 |

Instead of isolating the 2-chloro-5-(trichloromethyl)pyridine from this mixture, the above-described mixture is reacted with chlorine according to the conditions of the present invention as described herein to form 2,3-dichloro-5-(trichloromethyl)pyridine. The resulting 2,3-dichloro-5-(trichloromethyl)pyridine is separated from the reaction mixture by distillation, crystal refining, recrystallization from a solvent or a combination thereof.

The present reaction can be characterized by the following chemical equation:

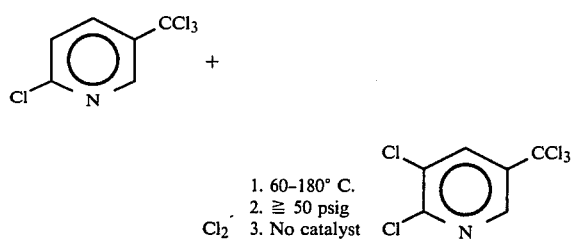

Preferred reactions are conducted at a temperature between about 140° C. and 160° C. and at a pressure between about 100 psig and 300 psig. An especially preferred reaction is conducted at about 150° C. and about 200 psig.

The following examples illustrate the practice of the present invention but should not be construed as limiting its scope. No attempt has been made to balance any chemical equations described herein.

A number of experiments were carried out as set forth in the following tables. In each experiment the starting material, 2-chloro-5(trichloromethyl)-pyridine was placed in the reactor and heated to the desired temperature after which chlorine gas was fed through a dip tube until the pressure reached 200 psig. Chlorine and, optionally, HCl were then metered into the reactor at the stated rates, with hydrogen chloride and excess chlorine being vented to a scrubber. The reaction mixtures were periodically sampled to monitor reaction progress.

TABLE I

| Run No. | Amount of Starting Material, Grams | Temp. °C. | Cl₂ Flow g/hr. | Reaction Time Hrs. | (A) | (B) | (C) | (D) | Other | Ratio B/C |
|---|---|---|---|---|---|---|---|---|---|---|
| 1 | 779.9 | 100 | 12.1 | 28.4 | 18 | 38.5 | — | 1.4 | 42.1 | ∞ |
| 2 | 701.5 | 125 | 22.2 | 65.8 | 34.5 | 27.5 | 0.2 | 3.8 | 34.0 | 138 |
| 3 | 691.9 | 150 | 21.9 | 27.5 | 46.3 | 30.0 | 1.7 | 2.5 | 19.5 | 18 |
| 4 | 618.9 | 150 | 21.5 | 22 | 47.2 | 31.4 | 1.9 | 2.5 | 17.0 | 17 |
| 5 | 781.8 | 150 | 12.8 | 44.5 | 28.4 | 49.5 | 2.1 | 3.5 | 16.5 | 24 |
| 6 | 706.3 | 160 | 18.5 | 33.7 | 43.7 | 43.8 | 4.1 | 4.0 | 4.4 | 11 |
| 7 | 703.6 | 175 | 23.6 | 33.2 | 37.1 | 41.1 | 14.5 | 5.7 | 1.6 | 2.8 |
| *8 | 706.1 | 200 | 31.9 | 18.2 | 21.3 | 24.7 | 39.7 | 8.1 | 6.2 | 0.6 |

Note:
Runs 1, 4 and 5 were carried out in a one liter, monel Parr reactor with a glass liner and a monel dip tube, sample tube and thermowell. The remaining runs were carried out in a 0.6 liter reactor constructed from a glass lined Pfaudler spool piece sealed at each end with a Teflon ® disk held in place by a stainless steel flange. The chlorine dip tube, sample tube and thermowell were tantalum. Run 5 was the only stirred reaction.
*Comparative Run.

TABLE II

| Run No. | Amount of Starting Material, Grams | Temp. °C. | Cl₂ Flow g/hr. | Wt % FeCl₃ | Reaction Time (Hrs.) | (A) | (B) | (C) | (D) | Other | Ratio B/C |
|---|---|---|---|---|---|---|---|---|---|---|---|
| 9 | 772.1 | 150 | 26.4 | 0.29 | 45 | 26.9 | 62.1 | 1.5 | 3.2 | 6.3 | 41 |
| 10 | 747.4 | 150 | 9.9 | 1.5 | 48 | 13.0 | 78.1 | 1.3 | 2.9 | 4.7 | 60 |
| 11 | 724.6 | 150 | 6.1 | 3.0 | 43 | 11.3 | 83.5 | 0.85 | 1.5 | 2.9 | 98 |
| 12* | 605 | 200 | 16.5 | 2.9 | 18 | 20.9 | 38.2 | 17.5 | 6.4 | 17.0 | 2.2 |

*Comparative run

TABLE III

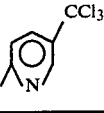

| Run No. | Amount of Starting Material, Grams | Temp. °C. | Cl₂ Flow g/hr. | HCl Flow g/hr. | Wt. % FeCl₃ | Reaction Time (Hrs.) | Production Composition (Weight %) (A) |
|---|---|---|---|---|---|---|---|
| 13 | 940.5 | 150 | 11.9 | 16.9 | 0 | 48 | 25.7 |
| 14 | 891.2 | 175 | 8.2 | 23.8 | 0 | 48 | 29.8 |
| 15 | 903.9 | 150 | 19.3 | 9.3 | 3.0 | 49 | 18.5 |
| 16* | 956.6 | 125 | 18.2 | 10.3 | 3.0 | 49 | 13.3 |

| Run No. | Production Composition (Weight %) (B) | (C) | (D) | Other | Ratio B/C |
|---|---|---|---|---|---|
| 13 | 71.8 | — | 1.8 | 0.7 | ∞ |
| 14 | 59.7 | 6.9 | 3.7 | — | 9 |
| 15 | 78.9 | — | 1.4 | 1.2 | ∞ |
| 16* | 83.7 | — | 0.4 | 2.6 | ∞ |

In similar operations, various pressure and temperature conditions as described herein are employed when reacting 2-chloro-5-(trichloromethyl)pyridine with an effective amount of Cl₂ in the absence of a catalyst resulting in the formation of 2,3-dichloro-5-(trichloromethyl)pyridine. The desired product can be isolated by distillation from the reaction mixture.

In other embodiments of the present invention, the reaction is conducted on a continuous recycle basis to prepare 2,3-dichloro-5-(trichloromethyl)pyridine. Such a process comprises the continuous, selective chlorination of 2-chloro-5-(trichloromethyl)pyridine at elevated temperature and pressure conditions as described herein. The 2,3-dichloro-5-(trichloromethyl)pyridine is recovered by distillation and any unreacted 2-chloro-5-(trichloromethyl)pyridine is recycled employing procedures well known in the art.

Starting Materials

The Cl₂ and 2-chloro-5-(trichloromethyl)pyridine are both well-known compounds. The Cl₂ is commercially available and 2-chloro-5-(trichloromethyl)pyridine can be prepared employing well-known procedures, such as, for example, the vapor phase chlorination of β-picoline according to procedures taught in U.S. Pat. Nos. 3,420,833; 4,205,175; and 4,241,213.

We claim:

1. A method of selectively chlorinating 2-chloro-5-(trichloromethyl)pyridine in the 3-position which comprises contacting 2-chloro-5-(trichloromethyl)pyridine in the liquid phase in the absence of a solvent with an effective amount of Cl₂ at a pressure of from about 50 to 1000 psig and a temperature of from about 125° C. to about 180° C. in the absence of a catalyst or in the absence of a catalyst other than FeCl₃ whereby the product contains 2,3-dichloro-5-(trichloromethyl)pyridine and 2,6-dichloro-3-(trichloromethyl)pyridine as the major components and the 2,3-dichloro-5-(trichloromethyl)pyridine is produced in a ratio to 2,6-dichloro-3-(trichloromethyl)pyridine of at least 2.8 to 1.

2. The method of claim 1 wherein an excess molar quantity of Cl₂ is employed, based on the molar quantity of 2-chloro-5-(trichloromethyl)pyridine.

3. The method of claim 2 wherein the pressure is at least about 100 psig and the temperature is at least about 100° C.

4. The method of claim 3 wherein the pressure is about 200 psig and the temperature is from about 140° C. to about 160° C.

5. The method of claim 4 wherein the temperature is about 150° C.

6. The method of claim 5 further comprising the step of isolating the 2,3-dichloro-5-(trichloromethyl)pyridine from the reaction mixture.

7. The method of claim 6 which is conducted as a batch operation.

8. The method of claim 6 which is conducted as a continuous, cyclical operation.

9. The method of claim 2 wherein the 2-chloro-5-(trichloromethyl)pyridine is supplied as a component in a mixture of chlorinated β-picolines and chlorinated pyridines.

10. The method of claim 9 wherein the mixture of chlorinated β-picolines and chlorinated pyridines is the reaction product mixture resulting from the vapor phase chlorination of β-picoline.

11. The method of claim 1 wherein HCl is continuously added to the reaction mixture.

* * * * *